United States Patent [19]

Pompni et al.

[11] Patent Number: 5,352,707
[45] Date of Patent: Oct. 4, 1994

[54] METHOD FOR TREATING AIRWAY CONGESTION

[75] Inventors: Shirley A. Pompni, Fort Pierce, Fla.; Vincent P. Gullo, Liberty Corner, N.J.; Ann C. Horan, Summit, N.J.; Mahesh G. Patel, Verona, N.J.; Stephen Coval, Clinton, N.J.

[73] Assignee: Harbor Branch Oceanographic Institution, Inc., Fort Pierce, Fla.

[21] Appl. No.: 857,889

[22] Filed: Mar. 26, 1992

[51] Int. Cl.$^5$ ............................................. A61K 31/135
[52] U.S. Cl. ...................................... 514/651; 514/826
[58] Field of Search ................................. 514/651, 826

[56] References Cited

PUBLICATIONS

Klaasen et al., ORL 50; 32–41 (1988).
Ishikawa et al., Nature, vol. 327, pp. 158–160, May 14, 1987.
Luo et al., European Journal of Pharmacology; 204 (1991) 331–314.
LaCroix et al., Br. J. Pharmacol., (1989), 97, 1075–1084.
Jackson; Otolaryngol Head Surg. 88:434–438 (Jul.–Aug.) 1980.
Simons et al.; Drugs 38 (2): 313-33 1989.
Christian et al; Journal of Physiology (1992), 457, pp. 407–430.
Gunasekera et al., Journal of Natural Products, vol. 52, No. 4, pp. 753–756 Jul.–Aug. (1989).
Cimino et al. Tetrahedron Letters, vol. 24, No. 29, pp. 3029–3032, 1983.
Xynas et al, Aust. J. Chem., (1989), 42, 1427–1433.

Primary Examiner—Marianne M. Cintins
Assistant Examiner—K. Weddington
Attorney, Agent, or Firm—Saliwanchik & Saliwanchik

[57] ABSTRACT

A method for treating airway congestion which comprises administering an effective amount of the compound of formula II which follows

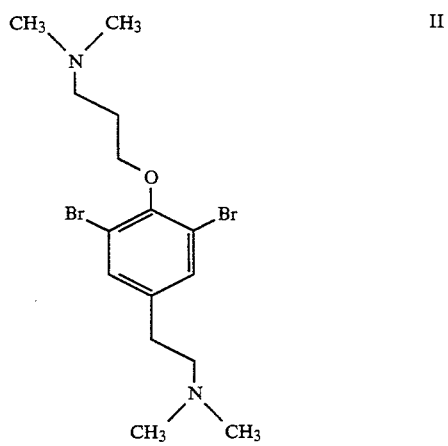

or a pharmaceutically acceptable salt thereof.

3 Claims, No Drawings

METHOD FOR TREATING AIRWAY CONGESTION

BRIEF SUMMARY OF THE INVENTION

The invention relates to a method for treating asthma, rhinitis, airway congestion, inflammation, cardiac arrhythmias, hypertension, hyper and hypo motility and acid secretion of the gastrointestinal tract, hypo and hyper activity of the central nervous system (CNS), migraine, and glaucoma which comprises administering an effective amount of the compound:

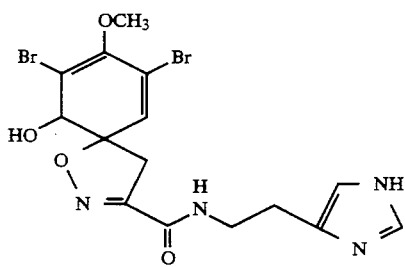

The invention also relates to a method for treating asthma, rhinitis, airway congestion, inflammation, cardiac arrhythmias, hypertension, hyper and hypo motility and acid secretion of the gastrointestinal tract, hypo and hyper activity of the central nervous system (CNS), migraine, and glaucoma which comprises administering an effective amount of the compound

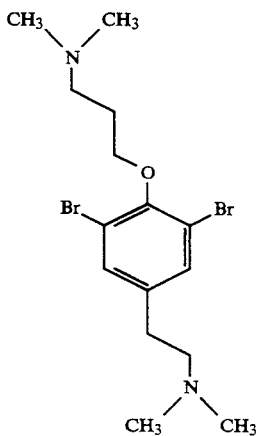

DETAILED DESCRIPTION OF THE INVENTION

A more complete understanding of the invention can be obtained by reference to preferred embodiments of the specific examples of the compounds, the compositions, and the methods of the invention. It will be apparent to those skilled in the art that the examples involve the use of materials and reagents that are commercially available from known sources, e.g., chemical supply houses, so no details are given respecting them.

The compounds of the invention are known. The compound of formula I is disclosed in the following two publications: Gunasekera et al, Journal of Natural Products, vol. 52, No. 4, pp 753–756, Jul.–Aug., (1989) and Cimino et al, Tetrahedron Letters, Vol. 24, No.29, pp. 3029–3032, (1983). The compound of formula II is disclosed in the following publication: Xynas et al, Aust. J. Chem., (1989), 42,1427–33. The just above mentioned three publications are herein incorporated by reference. The just above mentioned three publications do not disclose any biological activity for the compounds of the invention. These compounds may be obtained from marine sponges as described in the just-above cited publications.

These compounds have been given the following trivial names:
aerophobin-1 is the compound of formula I and
aplysamine-1 is the compound of formula II.

An alternative way of obtaining these compounds is by extracting the marine sponge *Verongula gigantea*.

Verongula gigantea

The compounds of formulas I and II can be prepared by extraction from the marine sponge *Verongula gigantea* of the phylum- Porifera, Class-Demospongiae, Order- Verongida, Family- Aplysinidae. A quantity of this sponge was collected at a depth of 210 meters on a flat sand bottom, north of Little Stirrup Cay, Bahama Islands, and at the coordinates: Latitude- 25° 50.68′ N, Longitude 77° 56.74′ W. The specimen (Harbor Branch Oceanographic Institution Division of Biomedical Research number 19-III-87-1-1) was collected using a manned submersible, which was equipped with a color video camera, 7-function manipulator arm, and collection buckets. The sample collected was then frozen and stored in freezers at −10° to −25° C.

The sample, which was not present in abundance at the collection site, was vase-shaped and yellow-purple in color; approximately 25% of the surface was covered with epibionts. A voucher specimen (catalog number 003:00406) is deposited at Harbor Branch Oceanographic Museum, Ft. Pierce, Fla. The voucher specimen is preserved in 70% ethanol with an expected shelf life of at least 30 years and is accessible to those skilled in the art for taxonomic identification purposes.

Descriptions of the marine sponge Verongula gigantea can be found in the published literature (e g Wiedenmayer F 1977. Shallow-water Sponges of the Western Bahamas. Experentia Suppl 28 pp 287 Birkhauser Verlag Basel & Stuttgart). The species is commonly found in the Bahama Islands and Caribbean at depths of 1–10 m. Its morphology is variable and it is described as hollow cylindrical, cup-shaped, vase-shaped, or bowl-shaped. This sample had become dislodged from the substrate and had tumbled into deeper water than it is normally found, however it was still alive at the time of collection.

Isolation of aerophobin-1

The extraction process which is set forth below follows FIG. 1.

A portion of the frozen sponge (19-III-87-1-1) was homogenized with ethanol in a blender, filtered, steeped in ethanol, and filtered. The resulting extracts were combined and concentrated under vacuum to give a brown gum. The gum was partitioned between ethyl acetate and water, and the ethyl acetate fraction subsequently extracted with 5% aqueous hydrochloric acid. After removal of the ethyl acetate layer the aqueous hydrochloric acid layer was treated with concentrated aqueous sodium hydroxide to adjust the pH to 9. The resulting alkaline solution was extracted with ethyl acetate, and the ethyl acetate extract concentrated under vacuum to give an oily residue.

The residue was chromatographed on silica gel employing gradient elution consisting of 2-20% methanol in dichloromethane. A group of fractions which eluted with approximately 5-15% methanol/dichloromethane, and which displayed H3 activity, were pooled. The residue from these combined fractions was subjected to gel filtration on Sephadex LH-20 with elution by 20:20:1 acetonitrile/dichloromethane/methanol to give pure aerophobin-1.

Aerophobin-1 has the follow physical characteristics:

FAB MS m/z (relative intensity): For (M+H)+ 479 (28), 477 (54), 475 (30).

HR FAB MS: Observed (M+H)+ 474.9612, calculated mass for $C_{15}H_{17}N_4O_4{}^{79}Br_2$ is 474.9616.

These data are consistent with literature data for Aerophobin-1.

Isolation of Aplysamine-1

The extraction process which is set forth below, follows FIG. 2.

A portion of the frozen sponge (19III-87-1-1), described above, was homogenized with ethanol in a blender, filtered, steeped in ethanol, and filtered. The resulting extracts were combined and concentrated under vacuum to give a brown/black semi-solid residue. The gum was partitioned between n-butanol and water. The residue from the n-butanol fraction was chromatographed on silica gel with elution by a gradient ranging from 0-50% methanol in dichloromethane. A group of fractions which eluted with approximately 35% methanol/dichloromethane showed H3 activity and were combined and concentrated to dryness under vacuum. This material was subjected to gel filtration on Sephadex LH-20 with elution by 1:1 methanol/chloroform to give pure aplysamine-1.

Aplysamine-1 has the following physical characteristics:

$^1$H NMR (CD$_3$OD): δ7.46 2H s, 4.02 2H t, 2.74 2H m, 2.67 2H m, 2.56 2Hm, 2.32 6H s, 2.96 6H s.

$^{13}$C NMR (CD$_3$OD): δ152.8 s, 140.5 s, 134.1 d, 119.0 s, 72.6 t, 61.6 t, 57.5 t, 45.4 q, 45.3 q, 33.2 t, 28.9 t.

FAB MS M/Z (relative intensity): for (M+H)+ 411 (55), 409 (100), 407 (60).

These data are consistent with literature data for aplysamine-1.

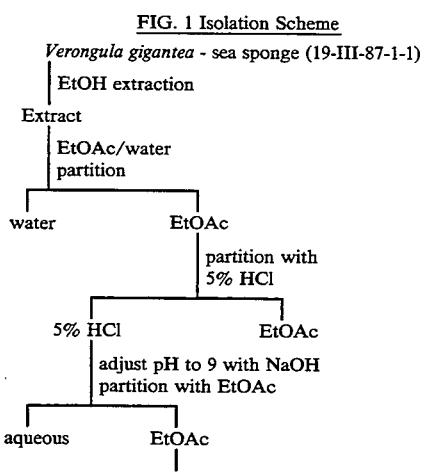

FIG. 1 Isolation Scheme
Verongula gigantea - sea sponge (19-III-87-1-1)

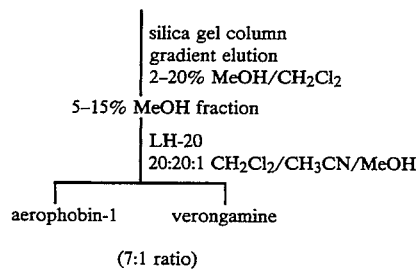

-continued
FIG. 1 Isolation Scheme

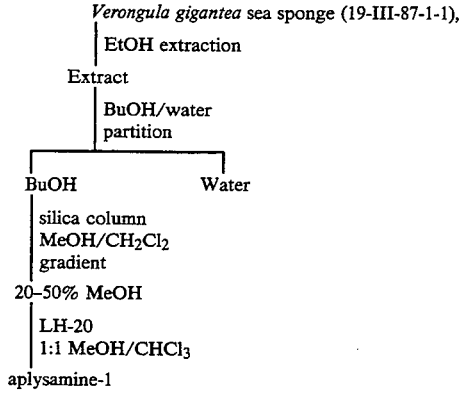

FIG. 2 Isolation Scheme
Verongula gigantea sea sponge (19-III-87-1-1),

The compounds of the invention may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms and are within the scope of this invention.

The following assay methods were used to illustrate the biological activities of the compounds of the invention.

H3 Receptor Binding Assay

The source of the H3 receptors in this experiment was guinea pig brain. The animals used weighed 400-600 g. The tissue was homogenized using a Polytron in a solution of 50 mM Tris, pH 7.5. The final concentration of tissue in the homogenization buffer was 10% w/v. The homogenates were centrifuged at 1000×g for 10 minutes in order to remove clumps of tissue and debris. The resulting supernatants were then centrifuged at 50,000×g for 20 minutes in order to sediment the membranes, which were next washed 3 times in homogenization buffer (50,000×g for 20 minutes each). The membranes were frozen and stored at −70° C. until needed.

All compounds to be tested were dissolved in DMSO (dimethyl sulfoxide) and then diluted into the binding buffer (50 mM Tris, pH 7.5) such that the final concentration was 2 μg/mL with 0.1% DMSO. Membranes were then added (400 μg of protein) to the reaction tubes. The reaction was started by the addition of 3 nM [$^3$H]R-α-methylhistamine (8.8 Ci/mmol) and incubated at 30° C. for 30 minutes. Bound ligand was separated from unbound ligand by filtration, and the amount of radioactive ligand bound to the membranes was quantitated by liquid scintillation spectrometry. All incubations were performed in duplicate and the standard error was less than 10% in all instances. A compound that inhibited greater than 50% of the specific binding of radioactive ligand to the receptor was serially diluted to determine its $IC_{50}$ (in μg/mL).

Guinea Pig Ileum Assay

Male guinea pigs (450–500 g) were sacrificed by cervical dislocation. Portions of the ileum (20–40 cm) were removed and placed in Tyrodes solution (NaCl, 8.0; KCl, 0.2; $MgCl_2.6H_2O$, 0.2; $CaCl_2$, 0.13; $NaH_2PO_4$, 0.06; dextrose, 1.0; $NaHCO_3$, 1.0 g/l). The ilea were cut into 2.5 cm segments, mounted between platinum wire coaxial electrodes and placed in water-jacketed organ baths containing 25 ml of the Tyrodes solution. Bath fluid temperature was maintained at 37° C. and aerated with 95% $O_2$–5%$CO_2$. The muscles were suspended from isometric force transducers (Grass FT023C) under 0.3 g resting tension. Contractions were amplified on a Buxco tension monitor and recorded on a Harvard polygraph. Monophasic rectangular-wave electrical pulses were delivered to the tissues every 60 seconds from a stimulator (model S-48, Grass Instruments Co.). The ileum segments were maximally stimulated with 3 volts at 40 Hz frequency and 1 mseconds duration in 1 pulse train every 60 seconds. The duration of 1 msecond was then decreased by 0.1 msecond until the size of the contraction reached 80% of the maximal response. Once this 80% response was determined it was evoked every 60 seconds throughout the experiment. All experiments were conducted with 1μM of chlorpheniramine present in the Tyrodes buffer.

Rα-methylhistamine inhibits the electrical field stimulated contractions of the guinea pig ileum and was used as the $H_3$ agonist reference standard. $H_3$ agonists were studied for their ability to inhibit the electrical field stimulated contractions and their activity was expressed as a percentage of the maximum Rα-methylhistamine effect. Agonists were tested by addition of logarithmically increasing doses to the bath fluid at intervals of 1 minute. Thioperamide is a competitive inhibitor of Rα-methylhistamine activity and was used as the $H_3$ antagonist reference standard. Antagonists were tested for their ability to inhibit Rα-methylhistamine and were added to the bath 5 minutes before generating an Rα-methylhistamine concentration-response curve.

Relative potency for agonists was determined from the pD2 calculations (Furchgott, R.F., The Pharmacology of Vascular Smooth Muscle. Pharm. Rev. 7, 183, 1955.) on 5 separate tissues. Relative potency for antagonists was determined from pA2 calculations (See Furchgott, above) on 15 separate tissues.

| Compound | Results $H_3$ receptor Binding $IC_{50}$ | Guinea Pig Ileum |
|---|---|---|
| Aerophobin-1 | 4.3 μg/ml | not active at 1 μg/ml |
| Aplysamine-1 | 0.34 μg/ml | antagonist at 1 μg/ml |

The above results demonstrate that the two compounds of the invention are active in the $H_3$ receptor assay. These results also demonstrate that aplysamine-1 alone was active on the guinea pig ileum as an $H_3$-antagonist. The two compounds of the invention are useful as agents in the treatment of asthma, rhinitis, airway congestion, inflammation, cardiac arrhythmias, hypertension, hyper and hypo motility and acid secretion of the gastrointestinal tract, hypo and hyper activity of the central nervous system (CNS), migraine, and glaucoma.

Therapeutic application of the compounds of formulas I and II and compositions containing them, can be contemplated to be accomplished by any suitable therapeutic method and technique presently or prospectively known to those skilled in the art.

In accordance with the invention, pharmaceutical compositions comprise, as the active ingredient, an effective amount of a compound of the invention and one or more non-toxic, pharmaceutically acceptable carriers or diluents. Examples of such carriers for use in the invention include ethanol, dimethyl sulfoxide, glycerol, silica, alumina, starch equivalent carriers and diluents.

While effective amounts for therapeutic treatment may vary, as conditions in which such compositions are used vary, a minimal dosage required for therapeutic activity is generally between 1 and 1000 milligrams one to four times daily.

Compounds of the invention can be administered as tablets, solutions, capsules, suspensions or aerosols. They can be administered orally, subcutaneously, intravenously, or by inhalation.

What is claimed is:

1. A method for treating airway congestion associated with histamine binding to a histamine $H_3$ receptor which comprises administering an effective amount of the compound

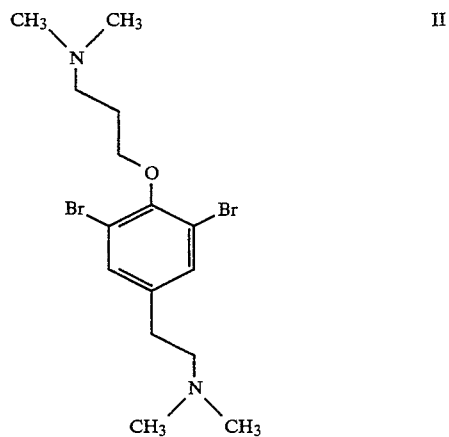

or a pharmaceutically acceptable salt thereof.

2. The method, according to claim 1, wherein said airway congestion is manifested as asthma.

3. The method, according to claim 1, wherein said airway congestion is manifested as rhinitis.

* * * * *

UNITED STATES PATENT AND TRADEMARK OFFICE
CERTIFICATE OF CORRECTION

PATENT NO. : 5,352,707

DATED : October 4, 1994

INVENTOR(S) : Pomponi *et al.*

It is certified that error appears in the above-indentified patent and that said Letters Patent is hereby corrected as shown below:

On the Title Page, under item [19] and item [75], delete "Pompni" and insert --Pomponi--.

Column 3, line 10: After "pure aerophobin-1." insert --Also obtained is verongamine which is described in U.S. Patent No. 5,217,986, issued June 8, 1993.--

Column 3, line 42: Delete "2.56 2Hm," and insert --2.56 2H m,--

Column 5, line 24: Delete "CaCl2  0.13; NaH2PO4  " and insert --CaCl2, 0.13; CaCl$_2$, 0.13; NaH$_2$PO$_4$, Signed and Sealed this Seventeenth Day of January, 1995

*Attest:*

BRUCE LEHMAN

*Attesting Officer*    *Commissioner of Patents and Trademarks*